United States Patent [19]

Weetall

[11] 4,245,038

[45] Jan. 13, 1981

[54] DETECTION OF NEISSERIA BACTERIA BY IMMUNOASSAY

[75] Inventor: Howard H. Weetall, Big Flats, N.Y.

[73] Assignee: Corning Glass Works, Corning, N.Y.

[21] Appl. No.: 837,364

[22] Filed: Sep. 28, 1977

[51] Int. Cl.³ .............................................. C12Q 1/66
[52] U.S. Cl. ........................................ 435/7; 424/12; 23/230 B
[58] Field of Search ............................. 435/7; 424/12; 23/230 B

[56] References Cited

U.S. PATENT DOCUMENTS

| | | | |
|---|---|---|---|
| 3,875,011 | 4/1975 | Rubenstein et al. | 435/7 |
| 3,974,269 | 8/1976 | Maley | 435/7 |
| 4,029,756 | 6/1977 | Gaafar | 435/7 |
| 4,066,744 | 1/1978 | Price et al. | 23/230 B |

*Primary Examiner*—Alvin E. Tanenholtz
*Attorney, Agent, or Firm*—Clinton S. Janes, Jr.; William E. Maycock

[57] ABSTRACT

This invention is concerned with means for determining the presence of Neisseria bacteria in a fluid sample, the method contemplating the release of an enzyme from the bacteria upon lysis which can be detected via the use of antibodies specific to the enzyme. Thus, inhibition of enzyme activity resulting from the presence of antibodies specific to the enzyme can be readily monitored. The enzyme released from the bacteria upon lysis is capable of oxidizing 1,2-propanediol and reducing nicotinamide-adenine-dinucleotide (NAD). The full structure of the enzyme is not understood but, because of those two substantive characteristics, the enzyme has been denominated 1,2-propanediol dehydrogenase. In sum, the instant invention combines the sensitivity of an enzymatic reaction with the specificity of an immunoassay.

11 Claims, No Drawings

DETECTION OF NEISSERIA BACTERIA BY IMMUNOASSAY

Related Applications

Patent Application Ser. No. 837,366, filed of even date by the present applicant entitled "Detecting Neisseria Bacteria", now U.S. Pat. No. 4,166,765 Patent Application Ser. No. 837,365, filed of even date by the present applicant entitled "Comparative Test for Neisseria", now U.S. Pat. No. 4,111,752 Patent Application Ser. No. 837,363, filed of even date by the present applicant entitled "Immunoassay of Neisseria Bacteria Via $(NH_4)_2SO_4$ Precipitation", Patent Application Ser. No. 837,360, filed of even date by the present applicant entitled "Immunological Detection of Neisseria Bacteria Via Labelled Antibodies", now U.S. Pat. No. 4,188,371 Patent Application Ser. No. 837,360, filed of even date by H. C. McDonald entitled "Detection and Quantitation of Neisseria Via Radioimmunoassay of an Enzyme Present in Neisseria Bacteria", and Patent Application Ser. No. 837,361, filed of even date by M. M. Takeguchi and H. H. Weetall entitled "Transport System for Clinical Specimens", now U.S. Pat. No. 4,150,950, each of said applications being assigned to the assignee of the instant application.

BACKGROUND OF THE INVENTION

This disclosure is concerned generally with means for determining the presence of Neisseria bacteria utilizing an immunoassay technique.

The importance of being able to quickly and accurately detect the presence of Neisseria bacteria, especially *Neisseria gonorrhoeae*, is well recognized. Conventional tests for detecting the presence of organisms such as *N. gonorrhoeae* involve the preparation of bacteria cultures or the use of serological methods. Such tests, however, have known limitations. See, for example, the publication "International Symposium on Gonorrhea", B. B. Diena, Ed., a collection of papers presented at the October, 1973 International Symposium on Gonorrhoea sponsored by the Health Protection Branch, Health and Welfare Canada, Ottawa, especially at p. 34 et seq.

A relatively simple and quick test for the presence of Neisseria in liquid samples which has been discovered is disclosed in the related application cited above entitled "Detecting Neisseria Bacteria". That test is founded upon the discovery of an enzyme in Neisseria bacteria which appears to be specific to Neisseria. The complete structure of the enzyme has not as yet been determined and no identification therefor has been located in the literature. However, the enzyme has been observed to oxidize 1,2-propanediol and reduce nicotinamide-adenine-dinuclectide (NAD). Tha behavior has led to the name 1,2-propanediol dehydrogenase being applied thereto, and that designation will be employed throughout this specification.

That a biochemical reaction can take place between an antigen and its homologous antibody giving rise to an antibody-antigen complex is well recognized. An explanation of that phenomenon can be found in "Immunochemistry of Enzymes and Their Antibodies", M. J. Salton, John Wiley & Sons, New York (1977). In the case of an enzyme, the reaction thereof with its specific antibody may result in inhibition of the activity displayed by the enzyme. In this manner, then, the presence of a particular enzyme can be detected by bringing the antibody specific to the said enzyme into contact with the sample in question and monitoring the result for a decrease in enzyme activity.

The instant invention contemplates the use of antibodies directed against the enzyme present in Neisseria bacteria, i.e., the 1,2-propanediol dehydrogenase referred to above, to inhibit enzyme activity in an assay sample, thereby inferring antibody specificity on the assay of the enzyme. This procedure combines the sensitivity of an enzymatic reaction with the specificity of an immunoassay.

SUMMARY OF THE INVENTION

The method of the invention consists of the following six general steps:
(1) preparing a lysate of the sample to be tested;
(2) preparing an antiserum specific to 1,2-propanediol dehydrogenase;
(3) combining the lysate and antiserum;
(4) incubating the mixture of lysate and antiserum;
(5) adding buffer, NAD, and 1,2-propanediol to the incubated mixture; and then
(6) testing for inhibition of activity of 1,2-propanediol dehydrogenase.

When the antiserum is combined with the lysate and the mixture incubated to permit reaction to take place between the antibodies and the enzyme, inhibition of the activity of the enzyme released during lysis will occur. Detection of this reduction in enzyme activity can be secured utilizing such conventional techniques as fluorometry and spectrophotometry. A quantitative measure of enzyme present can be had through such conventional methods as fluoroimmunoassay, radioimmunoassay, and dipstick.

Spectrophotometry provides a relatively simple and quick means for detecting enzyme activity and in the following examples the testing was conducted spectrophotometrically utilizing observations of molar absorbency at 340 nm.

Whereas the inventive method is operable with other species of Neisseria bacteria, the working examples reported below were directed specifically to *N. gonorrhoeae*.

SPECIFIC EMBODIMENTS

In the first step, a sample, e.g., human body fluid or exudate, is subjected to a conventional cellular lysing agent to release intracellular contents, including enzymes. The lysing procedure need only be conducted under such conditions that denaturing of any enzymes is avoided.

A method for preparing an operable lysate is disclosed in the above-cited related application entitled "Detecting Neisseria Bacteria" and that method was also employed here. Thus, a suspension of bacteria was prepared in 0.03 M TRIS buffer, pH 9.0. The suspension was compounded so as to contain approximately $10^5$ bacteria, as indicated via an absorbency of 0.1 on a Spec 20 spectrophotometer. To five milliliters of the suspension was added 0.5 ml of a 0.1% solution of egg-white lysozyme (Biozyme Laboratories) prepared in 0.03 M TRIS buffer, pH 9.0. This bacteria-buffer-lysozyme mixture was briefly mixed together and thereafter allowed to stand for two minutes at room temperature (about 23° C.). 0.5 ml of a 0.1% solution of EDTA (ethylene diamine tetraacetic acid) in 0.03 M TRIS buffer, pH 9.0, was then added and tubes containing the resultant mixture agitated in a shaker bath for 10 minutes at 12 reciprocating cycles/five seconds. The EDTA acts as a chelating agent to bond with any divalent metal ion present which might interfere with the activity of the enzyme. Other chelating agents may be used so long as the bacteria-buffer-lysozyme reaction is not adversely affected. Hence, the inclusion of EDTA is not mandatory but is a useful precaution. Finally, the mixtures were centrifuged for 10 minutes at 5000 rpm and the supernatant decanted off. This supernatant comprises the lysate.

An antiserum is prepared in the known manner which can be used as such or in the form of a globulin fraction of the antibody. In the immediately succeeding examples, separate quantities of antibody globulin (Ab) and non-specific globulin (NSG) were prepared. 0.1 ml of the globulin component was added to a 12×75 mm plastic tube containing 0.1 ml of the lysate. The total globulin concentration was 2.36 mg/ml and the lysate concentration 1.61 IU/ml. The sample was incubated for a stated period of time at 23° C. at pH 8.5 and then assayed.

To the mixture of lysate and globulin at room temperature (23° C.) were added 2.65 ml of 0.1 M TRIS buffer, pH 9.0, 0.1 ml (10 mg/ml) NAD, and 0.05 ml 1,2-propanediol.

A Perkin-Elmer double beam spectrometer was utilized to examine the samples at 340 nm, the results being reported in the table below. In the table, one unit of activity represents a change in optical density of 0.01 units/minute.

| Sample | Incubation Time | Units of Activity | % Inhibition |
|---|---|---|---|
| Lysate | 0 | 4 | 0 |
| Lysate | 0 | 4 | 0 |
| Lysate + 0.1 ml Ab | 10 minutes | 4 | 0 |
| Lysate + 0.1 ml NSG | 10 minutes | 4 | 0 |
| Lysate + 0.1 ml Ab | 30 minutes | 4 | 15 |
| Lysate + 0.1 ml NSG | 30 minutes | 5 | 0 |
| Lysate + 0.1 ml Ab | 60 minutes | 5 | 23 |
| Lysate + 0.1 ml NSG | 60 minutes | 6.75 | 0 |
| Lysate + 0.1 ml Ab | 120 minutes | 5 | 38 |
| Lysate + 0.1 ml NSG | 120 minutes | 8 | 0 |

Significant inhibition of enzyme activity is evident after about one hour.

In the following group of examples, 0.1 ml of globulin was incubated at room temperature with 0.1 ml lysate which had been buffered with 0.01 M borate buffered saline (BBS) to pH 8.5. The globulin concentration was either 0.12 mg/ml or 1.2 mg/ml. The lysate concentration was 1.61 IU/ml. The assay conditions employed were the same as those utilized above, viz., 2.65 ml 0.1 M TRIS, pH 8.0, 0.10 ml (10 mg/ml) NAD, and 0.05 ml 1,2-propanediol. The following table sets out the results of the several assays.

| Sample | Incubation Time | Units of Activity | % Inhibition |
|---|---|---|---|
| Lysate | 15 minutes | 8.0 | 0 |
| Lysate | 15 minutes | 10.0 | 0 |
| Lysate + 1.2 mg Ab | 24 minutes | 2.0 | 76 |
| Lysate + 1.2 mg NSG | 27 minutes | 8.0 | 6 |
| Lysate + 0.12 mg Ab | 30 minutes | 6.5 | 23.5 |
| Lysate + 0.12 mg NSG | 33 minutes | 8.0 | 6 |
| Lysate + 1.2 mg Ab | 61 minutes | 2.0 | 76 |
| Lysate + 1.2 mg NSG | 58 minutes | 8.0 | 0 |
| Lysate + 0.12 Ab | 64 minutes | 6.0 | 29 |
| Lysate + 0.12 mg NSG | 67 minutes | 9.0 | 0 |
| Lysate + 0.12 mg Ab | 144 minutes | 6.5 | 23.5 |
| Lysate + 0.12 mg NSG | 150 minutes | 9.0 | 0 |
| Lysate + 1.2 mg Ab | 141 minutes | 1.2 | 91 |
| Lysate + 1.2 mg NSG | 138 minutes | 7.0 | 18.7 |

Definite inhibition is obvious at the high concentrations of globulin utilized in the above examples. Nevertheless, there appears to be some slight autoinactivation of the enzyme after about two hours incubation at room temperature.

In the following set of examples, 0.1 ml of globulin was incubated at room temperature with 0.1 ml lysate which had been buffered with 0.01 M BBS to pH 7.6. The globulin concentration was either 12 mg/ml or 1.2 mg/ml and the lysate concentration 1.61 IU/ml. The assay was carried in a similar manner to the above except at a pH 7.5 rather than 9.0. Hence, the assay components consisted of 2.65 ml 0.5 M TRIS, pH 7.5, 0.10 ml (10 mg/ml) NAD, and 0.05 ml 1,2-propanediol. The results of the assays are recorded below.

| Sample | Incubation Time | Units of Activity | % Inhibition |
|---|---|---|---|
| Lysate | 70 minutes | 5.5 | 0 |
| Lysate + 1.2 mg Ab | 73 minutes | 1.0 | 82 |
| Lysate + 1.2 mg NSG | 75 minutes | 5.0 | 9 |
| Lysate + 0.12 mg Ab | 78 minutes | 4.0 | 27 |
| Lysate + 0.12 mg NSG | 80 minutes | 6.0 | 0 |
| Lysate + 1.2 mg Ab | 126 minutes | 1.0 | 82 |
| Lysate + 1.2 mg NSG | 130 minutes | 4.0 | 27 |
| Lysate + 0.12 mg Ab | 134 minutes | 4.0 | 27 |
| Lysate + 0.12 mg NSG | 135 minutes | 6.0 | 0 |

An examination of the above values indicates that at pH 7.6 greater inhibition of enzyme activity takes place initially but that phenomenon does not continue into the second hour of incubation. Furthermore, it appears that some auto-denaturation or autoinactivation of the enzyme occurs after an incubation period of about one hour.

In general, the operable pH values vary between about 7-10 with the optimum seeming to range about 9-10. Incubation can occur at temperatures approaching 0° C., but reaction between the antibodies and the enzyme contained within the lysate is expedited as the temperature of the antiserum-lysate mixture is raised to an optimum of about 50° C. The rate of reaction at room temperature, however, is sufficiently rapid to justify the convenience of operating thereat.

The following examples utilized whole antiserum instead of the globulin fraction. In order to increase sensitivity, the concentration of the NAD was raised to 10 mg/ml and the lysate used in the previous examples (1.61 IU/ml) was diluted 1:10 with 0.01 M BBS, pH 8.5. The serum dilutions were also made with BBS.

To 0.1 ml of diluted lysate was added 0.1 ml of whole antiserum at a dilution from 0 to 1:8. The 0.2 ml mixture was incubated for 40 minutes at room temperature. Two control samples of diluted lysate and buffer were also prepared.

The assay was carried out by first combining 2.65 ml 0.1 M TRIS, pH 9.0, with 0.10 ml (10 mg/ml) NAD, and 0.05 ml 1,2-propanediol. That combination was then added to the incubated mixture at room temperature and poured into a cuvette for examination at 340 nm.

| Sample | Units of Activity | % Inhibition |
|---|---|---|
| Control | 8 | 0 |
| Control | 8 | 0 |
| Undiluted Antiserum | 0.5 | 94 |
| 1:2 Dilution Antiserum | 1.2 | 85 |
| 1:4 Dilution Antiserum | 3.5 | 56 |
| 1:8 Dilution Antiserum | 5.7 | 29 |

It is quite apparent that inhibition of enzyme activity is achievable with whole serum as well as with the globulin fraction.

Therefore, a review of the above examples illustrates that an antibody directed specifically against the enzyme present in Neisseria bacteria, viz., 1,2-propanediol dehydrogenase, does indeed inhibit the activity of that enzyme. This circumstance confirms that the activity observed in an enzymatic assay is specific to the enzyme from the *N. gonorrhoea* organism.

It will be appreciated that the method disclosed hereinabove can be subject to numerous modifications and, accordingly, the exemplary embodiments reported ought to be considered as illustrative only with the scope of the invention being limited solely by the appended claims.

I claim:

1. A method for detecting the presence of Neisseria bacteria in a fluid sample consisting of bringing antibodies specific to 1,2-propanediol dehydrogenase released from said bacteria during lysis thereof into contact with a lysed sample and reacting said antibodies with said 1,2-propanediol dehydrogenase forming a 1,2-propanediol dehydrogenase-antibody complex, and then testing for inhibition of enzyme activity.

2. A method according to claim 1 wherein said fluid sample is a human body fluid or exudate.

3. A method according to claim 1 wherein said Neisseria bacteria are of the species *N. gonorrhoeae*.

4. A method for detecting Neisseria bacteria in a fluid sample, the method consisting of the steps:
   (a) preparing a lysate of said sample;
   (b) preparing an antiserum specific to 1,2-propanediol dehydrogenase;
   (c) combining said lysate and antiserum;
   (d) incubating the mixture of lysate and antiserum; and then
   (e) assaying the mixture for inhibition of activity of 1,2-propanediol dehydrogenase.

5. A method according to claim 4 wherein said fluid sample is a human body fluid or exudate.

6. A method according to claim 4 wherein said assay is carried out by:
   (a) adding buffer, NAD, and 1,2-propanediol to the incubated mixture of lysate and antiserum;
   (b) incubating said mixture; and then
   (c) testing for the inhibition of activity of 1,2-propanediol dehydrogenase spectrophotometrically.

7. A method according to claim 6 wherein the incubation of said lysate, antiserum, buffer, NAD, and 1,2-propanediol mixture is carried out at room temperature.

8. A method according to claim 7 wherein said incubation is carried out for about 0.5–2 hours.

9. A method according to claim 4 wherein said incubations are carried out at a pH between about 7–10.

10. A method according to claim 4 wherein said incubations are conducted at temperatures between about 0°–50° C.

11. A method according to claim 4 wherein said Neisseria bacteria are of the species *N. gonorrhoeae*.

* * * * *